United States Patent [19]

Jaquess et al.

[11] Patent Number: 5,866,016
[45] Date of Patent: Feb. 2, 1999

[54] METHODS AND COMPOSITIONS FOR CONTROLLING BIOFOULING USING COMBINATIONS OF AN IONENE POLYMER AND A SALT OF DODECYLAMINE

[75] Inventors: Percy A. Jaquess, Tigrett; Luis Fernando Del Corral, Memphis; Richard A. Clark, Collierville, all of Tenn.

[73] Assignee: Buckman Laboratories International, Inc., Memphis, Tenn.

[21] Appl. No.: 886,548

[22] Filed: Jul. 1, 1997

Related U.S. Application Data

[60] Provisional application No. 60/021,089, Jul. 2, 1996.
[51] Int. Cl.$^6$ .............. A01N 33/04; C02F 1/68; A61K 7/22
[52] U.S. Cl. .............. 210/764; 424/78.09; 424/78.1
[58] Field of Search .............. 424/78.09; 210/764; 422/14, 28

[56] References Cited

U.S. PATENT DOCUMENTS

| | | |
|---|---|---|
| Re. 28,808 | 5/1976 | Panzer et al. . |
| 2,957,785 | 10/1960 | Leatherland .............. 106/18.35 |
| 3,738,945 | 6/1973 | Panzer et al. . |
| 3,778,476 | 12/1973 | Rembaum et al. . |
| 3,874,870 | 4/1975 | Green et al. . |
| 3,894,946 | 7/1975 | Panzer et al. . |
| 3,894,947 | 7/1975 | Panzer et al. . |
| 3,930,877 | 1/1976 | Aitken . |
| 3,931,319 | 1/1976 | Green et al. . |
| 4,025,627 | 5/1977 | Green et al. . |
| 4,027,020 | 5/1977 | Green et al. . |
| 4,089,977 | 5/1978 | Green et al. . |
| 4,104,161 | 8/1978 | Wein . |
| 4,111,679 | 9/1978 | Shair et al. . |
| 4,147,627 | 4/1979 | Goodman . |
| 4,164,521 | 8/1979 | Goodman . |
| 4,166,041 | 8/1979 | Goodman . |
| 4,293,559 | 10/1981 | Buckman et al. . |
| 4,295,932 | 10/1981 | Pocius . |
| 4,506,081 | 3/1985 | Fenyes et al. . |
| 4,581,058 | 4/1986 | Fenyes et al. . |
| 4,606,773 | 8/1986 | Novak . |
| 4,769,155 | 9/1988 | Dwyer . |
| 4,778,813 | 10/1988 | Fenyes et al. . |
| 4,970,211 | 11/1990 | Fenyes et al. . |
| 5,051,124 | 9/1991 | Pera . |
| 5,093,078 | 3/1992 | Hollis et al. . |
| 5,128,100 | 7/1992 | Hollis et al. . |
| 5,142,002 | 8/1992 | Metzner . |

FOREIGN PATENT DOCUMENTS

| | | |
|---|---|---|
| 0 439 266 A | 7/1991 | European Pat. Off. . |
| 0 548 796 A | 6/1993 | European Pat. Off. . |
| 0 716 045 A | 6/1996 | European Pat. Off. . |
| WO 95 12976A | 5/1995 | WIPO . |

OTHER PUBLICATIONS

Delaquis et al., "Detachment Of *Pseudomonas fluorescens* From Biofilms On Glass Surfaces In Response To Nutrient Stress," Microb. Ecol. vol. 18, pp. 199–210 (1989).

Fletcher et al., "Influence Of Substratum Characteristics On The Attachment Of A Marine Pseudomonad To Solid Surfaces" Appl. Environ. Microbial. vol. 37, pp. 67–72 (1979).

Humphries et al., "The Effect Of A Range Biological Polymers And Synthetic Surfactants On the Adhesion Of A Marine Pseudomonas sp. Strain NCMB 2021 To Hydrophilic And Hydrophobic Surfaces" FEMS Microbiol. Ecol. vol. 38, pp. 299–308 (1986).

Humphries et al., "The Use Of Non–Ionic Ethoxylated And Propoxylated Surfactants To Prevent The Adhesion Of Bacteria To Solid Surfaces" FEMS Microbiology Letters vol. 42, pp. 91–101 (1987).

Kent, in "Biological Fouling: Basic Science and Models" (in Melo, L.F., Bott, T.R. Bernardo, C.A. (Eds.), Fouling Science and Technology, NATO ASI Series, Series E, Applied Sciences: No. 145, Kluwer Acad. Publishers, Dordrecht, The Nederlands 1988).

Starr et al., "UTEX—The culture collection of Algae at the University of Texas at Austin," J. of Phycology, vol. 29, pp. 90–91 (1993).

Rembaum "Biological Activity of Ionene Polymers" Applied Polymer Symp. vol. 22, pp. 299–317 (1973).

May, "Polymeric Antimicrobiol Agents" in Disinfection, Sterilization, and Preservation, S. Block (Ed.), pp. 322–333 (Lea & Febiger, Philadelphia, 1991).

*Primary Examiner*—Peter F. Kulkosky
*Attorney, Agent, or Firm*—Morgan, Lewis & Bockius LLP

[57] ABSTRACT

The present invention relates to a method to inhibit bacteria from adhering to a submergible surface. The method contacts the submergible surface with an ionene polymer and a salt of dodecylamine in a combined amount effective to inhibit bacterial adhesion to the submergible surface. The present invention also relates to a method for controlling biofouling of an aqueous system. This method adds an ionene polymer and a salt of dodecylamine in a combined amount effective to inhibit bacteria from adhering to a submerged surface within the aqueous system. This method effectively controls biofouling without substantially killing the fouling organisms. The present invention also relates to compositions containing an ionene polymer and a salt of dodecylamine and useable in the above methods. The compositions comprise an ionene polymer and a salt of dodecylamine in a combined amount effective to inhibit bacteria from adhering to submergible or submerged surfaces.

25 Claims, No Drawings

METHODS AND COMPOSITIONS FOR CONTROLLING BIOFOULING USING COMBINATIONS OF AN IONENE POLYMER AND A SALT OF DODECYLAMINE

This application is a provisional of 60/021,089 filed Jul. 2, 1996.

BACKGROUND OF THE INVENTION

1. Field of the Invention

The invention uses combinations of an ionene polymer and a salt of dodecylamine to inhibit bacterial adhesion to submergible or submerged surfaces, particularly those surfaces within an aqueous system. The invention also relates to methods and compositions for controlling biofouling.

2. Description of Related Art

Microorganisms adhere to a wide variety of surfaces, particularly surfaces in contact with aqueous fluids which provide a suitable environment for microbial growth. For example, microorganisms are known to adhere to ship hulls, marine structures, teeth, medical implants, cooling towers, and heat exchangers. Adhering to such submerged or submergible surfaces, microorganisms may foul the surface or cause it to deteriorate.

In mammals, (e.g., humans, livestock, pets), microorganisms adhered to a surface may lead to health problems. Plaque, for example, results from microorganisms adhering to the surfaces of teeth. Medical implants with unwanted microorganisms adhered to their surfaces often become crusted over and must be replaced.

Scientific studies have shown that the first stage of biofouling in aqueous systems is generally the formation of a thin biofilm on submerged or submergible surfaces, i.e., surfaces exposed to the aqueous system. Attaching to and colonizing on a submerged surface, microorganisms such as bacteria, are generally thought to form the biofilm and modify the surface to favor the development of a more complex community of organisms that makes up the advanced biofouling of the aqueous system and its submerged surfaces. A general review of the mechanisms and importance of biofilm as the initial stage in biofouling is given by C. A. Kent in "Biological Fouling: Basic Science and Models" (in Melo, L. F., Bott, T. R., Bernardo, C. A. (eds.), Fouling Science and Technology, NATO ASI Series, Series E, Applied Sciences: No. 145, Kluwer Acad. Publishers, Dordrecht, The Netherlands, 1988). Other literature references include M. Fletcher and G. I. Loeb, Appl. Environ. Microbiol 37 (1979) 67–72; M. Humphries et. al., FEMS Microbiology Ecology 38 (1986) 299–308; and M. Humphries et. al., FEMS Microbiology Letters 42 (1987) 91–101.

Biofouling, or biological fouling, is a persistent nuisance or problem in a wide variety of aqueous systems. Biofouling, both microbiological and macro biological fouling, is caused by the buildup of microorganisms, macro organisms, extracellular substances, and dirt and debris that become trapped in the biomass. The organisms involved include microorganisms such as bacteria, fungi, yeasts, algae, diatoms, protozoa, and macro organisms such as macro algae, barnacles, and small mollusks like Asiatic clams or Zebra Mussels.

Another objectionable biofouling phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and have a characteristic, undesirable odor that is different from that of the aqueous system in which it formed. The microorganisms involved in slime formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms.

Biofouling, which often degrades an aqueous system, may manifest itself as a variety of problems, such as loss of viscosity, gas formation, objectionable odors, decreased pH, color change, and gelling. Additionally, degradation of an aqueous system can cause fouling of the related water-handling system, which may include, for example, cooling towers, pumps, heat exchangers, and pipelines, heating systems, scrubbing systems, and other similar systems.

Biofouling can have a direct adverse economic impact when it occurs in industrial process waters, for example in cooling waters, metal working fluids, or other recirculating water systems such as those used in papermaking or textile manufacture. If not controlled, biological fouling of industrial process waters can interfere with process operations, lowering process efficiency, wasting energy, plugging the water-handling system, and even degrade product quality.

For example, cooling water systems used in power plants, refineries, chemical plants, air-conditioning systems, and other industrial operations frequently encounter biofouling problems. Airborne organisms entrained from cooling towers as well as waterborne organisms from the system's water supply commonly contaminate these aqueous systems. The water in such systems generally provides an excellent growth medium for these organisms. Aerobic and heliotropic organisms flourish in the towers. Other organisms grow in and colonize such areas as the tower sump, pipelines, heat exchangers, etc. If not controlled, the resulting biofouling can plug the towers, block pipelines, and coat heat-transfer surfaces with layers of slime and other biologic mats. This prevents proper operation, reduces cooling efficiency and, perhaps more importantly, increases the costs of the overall process.

Industrial processes subject to biofouling also include papermaking, the manufacture of pulp, paper, paperboard, etc. and textile manufacture, particularly water-laid nonwoven textiles. These industrial processes generally recirculate large amounts of water under conditions which favor the growth of biofouling organisms.

Paper machines, for example, handle very large volumes of water in recirculating systems called "white water systems." The furnish to a paper machine typically contains only about 0.5% of fibrous and non-fibrous papermaking solids, which means that for each ton of paper almost 200 tons of water pass through the headbox. Most of this water recirculates in the white water system. White water systems provide excellent growth media for biofouling microorganisms. That growth can result in the formation of slime and other deposits in headboxes, waterlines, and papermaking equipment. Such biofouling not only can interfere with water and stock flows, but when loose, can cause spots, holes, and bad odors in the paper as well as web breaks—costly disruptions in paper machine operations.

Biofouling of recreational waters such as pools or spas (including but not limited to hot tubs and jacuzzies) or decorative waters such as ponds or fountains can severely detract from people's enjoyment of them. Biofouling often results in objectional odors. More importantly, particularly in recreational waters, biofouling can degrade the water quality to such an extent that it becomes unfit for use and may even pose a health risk.

Sanitation waters, like industrial process waters and recreational waters, are also vulnerable to biofouling and its associated problems. Sanitation waters include toilet water, cistern water, septic water, and sewage treatment waters. Due to the nature of the waste contained in sanitation waters, these water systems are particularly susceptible to biofouling.

To control biofouling, the art has traditionally treated an affected water system with chemicals (biocides) in concentrations sufficient to kill or greatly inhibit the growth of biofouling organisms. See, e.g., U.S. Pat. Nos. 4,293,559 and 4,295,932. For example, chlorine gas and hypochlorite solutions made with the gas have long been added to water systems to kill or inhibit the growth of bacteria, fungi, algae, and other troublesome organisms. However, chlorine compounds may not only damage materials used for the construction of aqueous systems, they may also react with organics to form undesirable substances in effluent streams, such as carcinogenic chloromethanes and chlorinated dioxins. Certain organic compounds, such as methylenebisthiocyanate, dithiocarbamates, haloorganics, and quaternary ammonium surfactants, have also been used. While many of these are quite efficient in killing microorganisms or inhibiting their growth, they may also be toxic or harmful to humans, animals, or other non-target organisms.

One possible way to control the biofouling of aqueous systems, which include the associated submerged surfaces, would be to prevent or inhibit bacterial adhesion to submerged surfaces within the aqueous system. This can be done, of course, using microbicides which, however, generally suffer from some of the disadvantages mentioned above. As an alternative, the present invention provides methods and compositions useful to substantially inhibit bacterial adhesion to a submerged or submergible surface and to control biofouling of aqueous systems. The invention obviates the disadvantages of prior methods. Other advantages of this invention will become apparent from a reading of the specifications and appended claims.

SUMMARY OF THE INVENTION

The present invention relates to a method to inhibit bacteria from adhering to a submergible surface. The method contacts the submergible surface with an ionene polymer and a salt of dodecylamine in a combined amount effective to inhibit bacteria from adhering to a submergible surface.

The present invention relates also to a method for controlling biofouling of an aqueous system. This method adds to an aqueous system an ionene polymer and a salt of dodecylamine in a combined amount effective to inhibit bacteria from adhering to submerged surfaces within the aqueous system. This method effectively controls biofouling without substantially killing the bacteria.

The present invention also relates to a composition for controlling biofouling of an aqueous system. The composition comprises an ionene polymer and a salt of dodecylamine in a combined amount effective to inhibit bacteria from adhering to a submergible surface or a submerged surface within the aqueous system.

DETAILED DESCRIPTION OF THE INVENTION

In one embodiment, this invention relates to a method to inhibit bacteria from adhering to a submergible surface. A submergible surface is one which may at least partially be covered, overflowed, or wetted with a liquid such as water or another aqueous fluid. The surface may be intermittently or continually in contact with the liquid. As discussed above, examples of submergible surfaces include, but are not limited to ship or boat hulls, marine structures, teeth, medical implants, surfaces within an aqueous system such as the inside of a pump, pipe, cooling tower, or heat exchanger. A submergible surface may be composed of hydrophobic, hydrophilic, or metallic materials. Advantageously, using a combination of an ionene polymer and a salt of dodecylamine according to the invention can effectively inhibit bacteria from adhering to hydrophobic, hydrophilic, or metallic submergible or submerged surfaces.

To inhibit the adhesion of a bacteria to a submergible surface, the method contacts the submergible surface with an ionene polymer and a salt of dodecylamine. The mixture of an ionene polymer and a salt of dodecylamine is used in a combined amount effective to inhibit microorganism adhesion to the surface. The ionene polymer/dodecylamine salt combination may be applied to the submergible surface using means known in the art. For example as discussed below, the ionene polymer and dodecylamine salt may be applied, individually or together, by spraying, coating or dipping the surface with a liquid formulation containing the ionene polymer and/or the dodecylamine salt. Alternatively, the ionene polymer/dodecylamine salt combination may be formulated as a paste which is then spread or brushed on the submergible surface. Advantageously, the ionene polymer/dodecylamine salt combination may be a component of a composition or formulation commonly used with a particular submergible surface.

"Inhibiting bacteria from adhering" to a submergible surface means to allow a scant or insignificant amount of bacterial adhesion for a desired period of time. Preferably, essentially no bacterial adhesion occurs and more preferably, it is prevented. The combined amount of ionene polymer and salt of dodecylamine employed should allow only scant or insignificant bacterial adhesion and may be determined by routine testing. Preferably, the combined amount of ionene polymer and salt of dodecyl amine used is sufficient to apply at least a monomolecular film of the combination to the submergible surface. Such a film preferably covers the entire submergible surface.

Contacting a submergible surface with a combination of an ionene polymer and salt of dodecylamine according to this method allows the surface to be pretreated against bacterial adhesion. Accordingly, the surface may be contacted with such a combination then submerged in the aqueous system.

The present invention relates also to a method for controlling biofouling of an aqueous system. An aqueous system comprises not only the aqueous fluid or liquid flowing through the system but also the submerged surfaces associated with the system. Submerged surfaces are those surfaces in contact with the aqueous fluid or liquid. Like the submergible surfaces discussed above, submerged surfaces include, but are not limited to, the inside surfaces of pipes or pumps, the walls of a cooling tower or headbox, heat exchangers, screens, etc. In short, surfaces in contact with the aqueous fluid or liquid are submerged surfaces and are considered part of the aqueous system.

The method of the invention adds a combination of an ionene polymer and a salt of dodecylamine to the aqueous system in an amount which effectively inhibits bacteria from adhering to a submerged surface within the aqueous system.

At the concentration used, this method effectively controls biofouling of the aqueous system without substantially killing the bacteria.

"Controlling biofouling" of the aqueous system means to control the amount or extent of biofouling at or below a desired level and for a desired period of time for the particular system. This can eliminate biofouling from the aqueous system, reduce the biofouling to a desired level, or prevent biofouling entirely or above a desired level.

According to the present invention, "inhibiting bacteria from adhering" to a submerged surface within the aqueous system means to allow a scant or insignificant amount of bacterial adhesion for a desired period of time for the particular system. Preferably, essentially no bacterial adhesion occurs and more preferably, bacterial adhesion is prevented. Using an ionene polymer/dodecylamine salt combination according to the invention can, in many cases, break up or reduce other existing attached microorganisms to undetectable limits and maintain that level for a significant period of time.

While some ionene polymers and some salts of dodecylamine may exhibit biocidal activity at concentrations above certain threshold levels, a combination of an ionene polymer and a dodecylamine salt of the invention effectively inhibit bacterial adhesion at concentrations generally well below such threshold levels. According to the invention, the combination of an ionene polymer and a salt of dodecylamine inhibits bacterial adhesion without substantially killing the bacteria. Thus, the effective combined amount of an ionene polymer and a dodecylamine salt used according to the invention is below the toxic threshold, even if the combination also has biocidal properties. For example, the concentration of the combination may be ten or more times below its toxic threshold. Preferably, the combination should also not harm non-target organisms which may be present in the aqueous system.

A combination of an ionene polymer and a salt of dodecylamine may be used to control biofouling in a wide variety of aqueous systems such as those discussed above. These aqueous systems include, but are not limited to, industrial aqueous systems, sanitation aqueous systems, and recreational aqueous systems. As discussed above, examples of industrial aqueous systems are metal working fluids, cooling waters (e.g., intake cooling water, effluent cooling water, and recirculating cooling water), and other recirculating water systems such as those used in papermaking or textile manufacture. Sanitation aqueous systems include waste water systems (e.g., industrial, private, and municipal waste water systems), toilets, and water treatment systems, (e.g., sewage treatment systems). Swimming pools, fountains, decorative or ornamental pools, ponds or streams, etc., provide examples of recreational water systems.

The combined amount of an ionene polymer and a salt of dodecylamine effective to inhibit bacteria from adhering to a submerged surface in a particular system will vary somewhat depending on the aqueous system to be protected, the conditions for microbial growth, the extent of any existing biofouling, and the degree of biofouling control desired. For a particular application, the amount of choice may be determined by routine testing of various amounts prior to treatment of the entire affected system. In general, a combined amount used in an aqueous system may range from about 1 to about 500 parts per million and more preferably from about 20 to about 100 parts per million of the aqueous system.

Ionene Polymers

Ionene polymers or polymeric quaternary ammonium compounds (polyquats), i.e., cationic polymers containing quaternary nitrogens in the polymer backbone (also known as polymeric quats or polyquats), belong to a well-known class of compounds. The biological activity of this class of polymers is also known. See, e.g., A. Rembaum, *Biological Activity of Ionene Polymers*, Applied Polymer Symposium No. 22, 299–317 (1973) and O. May, "Polymeric Antimicrobial Agents" in *Disinfection, Sterilization, and Preservation*, S. Block, Ed., 322–333 (Lea & Febiger, Philadelphia, 1991), which are incorporated by reference. Ionene polymers have a variety of uses in aqueous systems such as microbicides, bactericides, and algicides as well as controlling, even preventing, biofilm and slime formation. U.S. Pat. Nos. 3,874,870, 3,931,319, 4,027,020, 4,089,977, 4,111,679, 4,506,081, 4,581,058, 4,778,813, 4,970,211, 5,051,124, 5,093,078, 5,142,002 and 5,128,100, which are incorporated here by reference, give various examples of these polymers, their preparation, and their uses.

Any ionene polymer or mixture of ionene polymers may be used to practice this invention. Ionene polymers may be classified according to the repeating unit found in the polymer. The repeating unit results from the reactants used to make the ionene polymer.

A first preferred type of ionene polymer comprises the repeating unit of formula I:

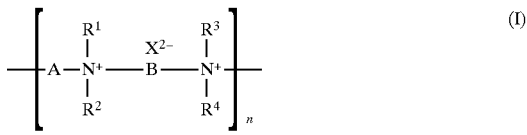

In this formula, $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, symmetric or asymmetric di-$C_1$–$C_{10}$-alkylenether, arylene, arylene-$C_1$–$C_{10}$-alkylene, or $C_1$–$C_{10}$-alkylenearyl-$C_1$–$C_{10}$ alkylene. Preferably, "A" is a divalent $C_1$–$C_5$ alkylene, $C_2$–$C_5$ alkenylene, $C_2$–$C_5$ hydroxyalkylene, or symmetric di-$C_2$–$C_5$-alkylenether, and most preferably "A" is —$CH_2CH_2CH_2$—, —$CH_2CH(OH)CH_2$— or —$CH_2CH_2OCH_2CH_2$—.

The group "B" is a divalent radical selected from $C_1$–$C_{10}$ alkylene, $C_2$–$C_{10}$ alkenylene, $C_2$–$C_{10}$ alkynylene, $C_1$–$C_{10}$ hydroxyalkylene, arylene, arylene-$C_1$–$C_{10}$-alkylene, or $C_1$–$C_{10}$-alkylenearyl-$C_1$–$C_{10}$-alkylene. Preferably, "B" is $C_1$–$C_5$ alkylene, $C_2$–$C_5$ alkenylene, $C_2$–$C_5$ hydroxyalkylene, arylene, arylene-$C_1$–$C_5$-alkylene, or $C_1$–$C_5$ alkylenearyl-$C_1$–$C_5$-alkylene. Most preferably "B" is —$CH_2CH_2$—, —$CH_2CH_2CH_2$—, —$CH_2CH_2CH_2CH_2$—, or —$CH_2(CH_2)_4CH_2$—.

The counter ion, $X^{2-}$, is a divalent counter ion, two monovalent counter ions, or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described in U.S. Pat. No. 3,778,476, the disclosure of which is incorporated here by reference.

The ionene polymers having the repeating unit of formula I may be prepared by a number of known methods. One method is to react a diamine of the formula R¹R²N-B-NR³R⁴ with a dihalide of the formula X-A-X. Ionene polymers having this repeating unit and methods for their preparation are described, for example, in U.S. Pat. Nos. 3,874,870, 3,931,319, 4,025,627, 4,027,020, 4,506,081 and 5,093,078, the disclosures of which are incorporated here by reference. The biological activity of ionene polymers having the repeating unit of formula I is also described in these patents.

Among the ionene polymers with a repeating unit of formula I, a particularly preferred ionene polymer is poly [oxyethylene-(dimethyliminio)ethylene(dimethyliminio) ethylene dichloride. In this ionene polymer of formula I, $R^1$, $R^2$, $R^3$ and $R^4$ are each methyl, A is —$CH_2CH_2OCH_2CH_2$—, B is —$CH_2CH_2$—, and $X^{2-}$ is 2 Cl⁻, and the average molecular weight is 1,000–5,000. This ionene polymer is available from Buckman Laboratories, Inc. of Memphis, Tenn. as BUSAN® 77 product or WSCP® product, which are each 60% aqueous dispersions of the polymer. BUSAN® 77 and WSCP® are biocides used primarily in aqueous systems, including metalworking fluids, for microorganism control.

Another particularly preferred ionene polymer having a repeating unit of formula I is the ionene polymer where $R^1$, $R^2$, $R^3$ and $R^4$ are each methyl, A is —$CH_2CH(OH)CH_2$—, B is —$CH_2CH_2$—, and $X^{2-}$ is 2 Cl⁻. This ionene polymer is a reaction product of N,N,N',N'-tetramethyl-1,2-ethanediamine with (chloromethyl)-oxirane, and has an average molecular weight of 1,000–5,000. The polymer is available from Buckman Laboratories, Inc. as BUSAN® 79 product and WSCP® II product, which are each 60% aqueous solutions of the polymer.

A second type of ionene polymer comprises the repeating unit of formula II:

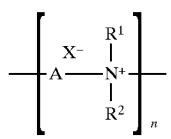

In formula II, the definitions of $R^1$, $R^2$, and A are the same as those defined above for formula I. X⁻ is a monovalent counter ion, one half of a divalent counter ion, or a fraction of a polyvalent counter ion sufficient to balance the cationic charge of the repeating unit which forms the ionene polymer. X⁻ may be, for example, a halide or trihalide anion, and X⁻ is preferably chloride or bromide.

The ionene polymers having the repeating unit of formula II may be prepared by known methods. One method is to react an amine of the formula R¹R²NH with a haloepoxide such as epichlorohydrin. Ionene polymers having the repeating unit of formula II are described, for example, in U.S. Pat. Nos. 4,111,679 and 5,051,124, the disclosures of which are incorporated here by reference. The biological activity of ionene polymers having the repeating unit of formula II is also described in these patents.

Preferred ionene polymers having the repeating unit of formula II are those where $R^1$ and $R^2$ are each methyl, A is —$CH_2CH(OH)CH_2$—, and X⁻ is Cl⁻. This polymer is obtained as a reaction product of N-dimethylamine with (chloromethyl)oxirane, and has an average molecular weight of 2,000–10,000. The polymer is available from Buckman Laboratories, Inc. as the BUSANO® 1055 product, a 50% aqueous dispersion of the polymer.

Another preferred ionene polymer having the repeating unit of formula II is obtained as a reaction product of dimethylamine with epichlorohydrin, where $R^1$ and $R^2$ are each methyl, A is —$CH_2CH(OH)CH_2$— and X⁻ is Cl⁻. This ionene polymer has a 5,000–10,000 average molecular weight, and is available from Buckman Laboratories, Inc. in a 50% aqueous solution as the BUSAN® 1055 product.

A third type of ionene polymer comprises a repeating unit of formula III:

wherein R is

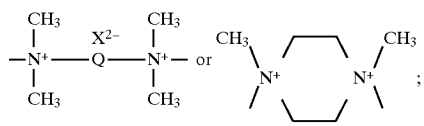

The group Q is —$(CHR')_p$—, —$CH_2$—CH=CH—$CH_2$—, —$CH_2$—$CH_2$—O—$CH_2$—$CH_2$—, —$CH_2$—CH(OH)—$CH_2$—, or —$(CHR')_n$—NH—C(O)—NH(CHR')$_n$—. The group B' is {—[$CH_2$—CH(OH)—$CH_2$—N⁺R'$_2$—(CHR')$_n$—NH—C(O)—NH]—, X⁻} or {—[(CHR')$_n$—N⁺R'$_2$—$CH_2$—CH(OH)—$CH_2$]—, X⁻}. The variables n and p independently vary from 2 to 12. Each R' is independently hydrogen or a $C_1$–$C_{20}$ alkyl group. $X^{2-}$ is a divalent counter ion, two monovalent counter ions, or a fraction of a polyvalent counter ion sufficient to balance the cationic charge in the group R. X⁻ is a monovalent counter ion, one half of a divalent counter ion or a fraction of a polyvalent counter ion sufficient to balance the cationic charge in the group B'. Preferably, R' is hydrogen or $C_1$–$C_4$ alkyl, n is 2–6, and p is 2–6. Most preferably, R' is hydrogen or methyl, n is 3 and p is 2. Preferred counter ions for $X^{2-}$ and X⁻ are the same as those discussed above for formulae I and II.

The polymers of formula III are derived by known methods from bis-(dialkylaminoalkyl) ureas, which are also known as urea diamines. Ionene polymers of the formula III, methods of their preparation, and their biological activities are described in U.S. Pat. No. 4,506,081, the disclosure of which is incorporated here by reference.

Preferred ionene polymers having the repeating unit of formula III are those where R is urea diamine and B' is $CH_2CH(OH)CH_2$, and X⁻ is Cl⁻. Available from Buckman Laboratories, Inc., ASTAT product and BL® 1090 product are 50% aqueous dispersions of this ionene polymer. The ionene polymer is obtained as a reaction product of N,N'-bis-[1-(3-(dimethylamino)-propyl)]urea and epichlorohydrin, such ionene polymer having an average molecular weight of 2,000–15,000, preferably 3,000–7,000.

Ionene polymers comprising the repeating units of formulae I, II, and III may also be cross-linked with primary, secondary or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking co-reactants, are disclosed in U.S. Pat. No. 3,738,945 and Reissue U.S. Pat. No. 28,808, the disclosures of which are incorporated here by reference. The Reissue Patent describes the cross-linking of ionene polymers prepared by the reaction of dimethylamine and epichlorohydrin. The cross-linking co-reactants listed are ammonia, primary amines, alkylenediamines, polyglycolamines, piperazines, heteroaromatic diamines and aromatic diamines.

U.S. Pat. No. 5,051,124, the disclosure of which is incorporated here by reference, describes cross-linked ionene polymers resulting from the reaction of dimethylamine, a polyfunctional amine, and epichlorohydrin. U.S. Pat. No. 5,051,124 also describes methods of inhibiting the growth of microorganisms using such cross-linked ionene polymers. Other examples of various cross-linked ionene polymers and their properties are provided in U.S. Pat. Nos. 3,894,946, 3,894,947, 3,930,877, 4,104,161, 4,164,521, 4,147,627, 4,166,041, 4,606,773, and 4,769,155. The disclosures of each of these patents is incorporated here by reference.

A preferred cross-linked ionene polymer has a repeating unit of formula II, where $R^1$ and $R^2$ are each methyl, A is —$CH_2CH(OH)CH_2$—, $X^-$ is $Cl^-$. The ionene polymer is cross-linked with ammonia. This ionene polymer has a molecular weight of approximately 100,000–500,000, and is available from Buckman Laboratories, Inc. in a 50% aqueous dispersion sold as the BL® 1155 product.

Buckman Laboratories, Inc. products BUSAN® 1099 or BUBOND® 65 are 25% aqueous dispersions of a cross-linked ionene polymer having repeating units of formula II, where $R^1$ and $R^2$ are each methyl, A is —$CH_2CH(OH)CH_2$—, $X^-$ is $Cl^-$, and the cross-linking agent is monomethylamine. This preferred ionene polymer has a molecular weight of approximately 10,000–100,000.

The ionene polymers comprising the repeating units of formulae I, II, or III may also be capped, i.e., have a specific end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S. Pat. Nos. 3,931,319 and 5,093,078, the disclosures of which are incorporated here by reference.

Salts of Dodecylamine

The salts of dodecylamine employed in the present invention preferably have the following general formula:

$C_{12}H_{25}NH_3^+Z^-$ in which Z is an anion or a fraction of a polyvalent counter ion sufficient to balance the cationic charge in the dodecylamine. Z is preferably the conjugate base of an organic or inorganic acid, i.e., Z is derived from an organic or inorganic acid by loss of an ionizable proton. Illustrative examples of suitable organic acids are the mono- and di-carboxylic acids; suitable inorganic acids include the hydrohalide acids, such as hydrochloric acid.

Preferably, Z is derived from an acyclic, cyclic, or aromatic mono- or dicarboxylic acid. The carboxylic acid preferably has up to ten carbon atoms. If cyclic or aromatic, the ring may contain one or more heteroatoms, such as N, O, or S.

The carboxylic acid may also be substituted by any suitable substituent that does not adversely effect the activity of the inventive compositions. Illustrative examples of suitable substituents include alkyl groups, substituted alkyl groups, alkenyl groups, substituted alkenyl groups, amino groups, oxo groups, halogen atoms, etc.

Illustrative examples of useful carboxylic acid groups include: acetyl, propionyl, citral, lactyl, valeryl, phthalyl, succinyl, octanoyl, nonanoyl, formyl, sorbyl, oxalyl, lauryl, and benzoyl. One of ordinary skill will recognize that other organic acid groups may also be used in the present invention.

The dodecyl group of the dodecylamine may be branched or unbranched, i.e., straight chain. Preferably, the dodecyl group is unbranched.

The dodecyl group may be unsubstituted or substituted by one or more substituents that do not adversely effect the activity of the inventive salts. Illustrative examples of suitable substituents include alkyl groups, alkenyl groups, alkoxy groups, aryl groups, aralkyl groups, hydroxy groups, oxo groups (to form a ketone), acid groups and derivatives thereof, such as esters and amides, and halogen atoms. Preferably, the dodecyl group is unsubstituted.

One or more of the hydrogen atoms bound to the nitrogen atom may be replaced by a suitable substituent to give a secondary, tertiary, or quaternary amine salt of dodecylamine. Preferably, a primary amine salt of dodecylamine is employed.

The following carboxylic acid salts of dodecylamine are particularly preferred in the practice of the present invention: dodecylamine acetate, dodecylamine propionate, dodecylamine butyrate, dodecylamine citrate, dodecylamine lactate, dodecylamine valerate, dodecylamine phthalate, dodecylamine succinate, dodecylamine octanoate, dodecylamine nonanate, dodecylamine formate, dodecylamine sorbate, dodecylamine oxalate, dodecylamine laurate, dodecylamine benzoate, dodecylamine 2-hydroxybenzoate, dodecylamine 3-hydroxybenzoate, or dodecylamine 4-hydroxybenzoate. More particularly preferred of these compounds are dodecylamine acetate, dodecylamine propionate, dodecylamine butyrate, dodecylamine valerate, dodecylamine phthalate, dodecylamine succinate, dodecylamine citrate, and dodecylamine lactate. Most particularly preferred is dodecylamine acetate.

The salts of dodecylamine are preferably prepared by reacting dodecylamine with the desired acid in the presence of a suitable solvent. Suitable acids groups are available in their acid or salt form either commercially from laboratory supply houses or can be prepared from readily available starting materials using well-known literature methods.

The synthesis of the amine salts generally can be carried out in a solvent which may be a solvent for at least one of the reactants but which is generally a solvent for the desired product. Preferred solvent systems include inorganic acids and organic acids or alcohols. Most preferred is acetic acid.

The temperature of reaction may be readily determined by one skilled in the art depending on the particular reactants employed. Preferably the temperature of reaction varies from 40° C. to 110° C. or more, more preferably the temperature of the reaction is between 70° C. and 100° C. The reaction is allowed to proceed until complete, as shown, for example, by a pH meter (the reaction is complete when the pH meter indicates that the limiting reactant has been neutralized). Generally, the reaction is stirred for 30 min to 2 hours, preferably for about 1 to 2 hours.

After the reaction is complete, the reaction product can be worked up using well-known techniques to isolate and purify the desired salt of dodecylamine. Excess reactants and any solids formed during the reaction can be filtered off, and the filtrate evaporated to yield the crude product. In cases where the desired salt compound is a solid, the product of the reaction may be recrystallized from an appropriate solvent to yield a more pure compound. It should be noted, however, that both pure and crude salts of dodecylamine can be used for in the compositions and methods of this invention. The preparation of the salts is not limited to the exact process or steps described above. Any of procedures known to the art which yield the desired end product may be used.

The particular ionene polymer or salt of dodecylamine employed may be selected based on the compatibility of these compounds with the submergible surface or aqueous system. Compatibility is determined by criteria such as solubility in the aqueous system and lack of reactivity with the surface or system in question. The compatibility is readily determined by one of ordinary skill by adding the ionene polymer or salt of dodecylamine to the material or media to be used. When used in an aqueous system, it is preferable that the ionene polymer and/or salt of dodecylamine be freely soluble in the system.

As described above, an ionene polymer and a salt of dodecylamine are used in a combined amount effective to inhibit bacteria from adhering to a submergible surface. This preferably is a synergistically effective amount. The weight ratios of ionene polymer to salt of dodecylamine may vary depending on the type of aqueous system or surface to which the combination is applied. One skilled in the art can readily determine without undue experimentation, the appropriate weight ratios for a specific application. The weight ratio of ionene polymer to salt of dodecylamine preferably ranges from 1:99 to 99:1, more preferably from 1:30 to 30:1, and most preferably 1:2 to 2:1.

Depending upon the specific application, a composition containing an ionene polymer and a salt of dodecylamine may be prepared in liquid form by dissolving either or both in water or in an organic solvent, or in dry form by adsorbing onto a suitable vehicle or it can be compounded into a tablet form. The combination may be prepared in an emulsion form by emulsifying it in water, or if necessary, by adding a surfactant.

The methods according to the invention may be part of an overall water treatment regimen. The combination of an ionene polymer and a salt of dodecylamine may be used with other water treatment chemicals, particularly with biocides (e.g., algicides, fungicides, bactericides, molluscicides, oxidizers, etc.), stain removers, clarifiers, flocculants, coagulants, or other chemicals commonly used in water treatment. For example, submergible surfaces may be contacted with a combination of an ionene polymer and a salt of dodecylamine as a pretreatment to inhibit bacterial adhesion and placed in aqueous system using a microbicide to control the growth of microorganisms. Or, an aqueous system experiencing heavy biological fouling may first be treated with an appropriate biocide to overcome the existing fouling. A combination of an ionene polymer and a salt of dodecylamine may then be employed to maintain the aqueous system. Alternatively, a combination of an ionene polymer and a salt of dodecylamine may be used together with a biocide to inhibit bacteria from adhering to submerged surfaces within the aqueous system while the biocide acts to control the growth of microorganisms in the aqueous system. This generally allows less microbicide to be used.

"Controlling the growth of the microorganisms" in an aqueous system means control to, at, or below a desired level and for a desired period of time for the particular system. This can be eliminating the microorganisms or preventing their growth in the aqueous systems.

The combination of an ionene polymer and a salt of dodecylamine may be used in the methods of the invention as a solid or liquid formulation. Accordingly, the present invention also relates to a composition containing a combination of an ionene polymer and a salt of dodecylamine. The composition comprises an ionene polymer and a salt of dodecylamine in a combined amount effective to inhibit bacteria from adhering to a submergible surface or a submerged surface within an aqueous system. When used in combination with another water treatment chemical such as a biocide, the composition may also contain that chemical. If formulated together, the ionene polymer, salt of dodecylamine, and water treatment chemical should not undergo adverse interactions that would reduce or eliminate their efficacy in the aqueous system. Separate formulations are preferred where adverse interactions may occur.

Depending on its use, a composition according to the present invention may be prepared in various forms known in the art. For example, the composition may be prepared in liquid form as a solution, dispersion, emulsion, suspension, or paste; a dispersion, suspension, or paste in a nonsolvent; or as a solution by dissolving the ionene polymer or salt of dodecylamine in a water, an organic solvent, or combination of water and/or solvents. Suitable solvents include, but are not limited to, acetone, glycols, alcohols, ethers, or other water-dispersible solvents. Aqueous formulations are generally preferred.

The composition may be prepared as a liquid concentrate for dilution prior to its intended use. Common additives such as surfactants, emulsifiers, dispersants, and the like may be used as known in the art to increase the solubility of the ionene polymer, salt of dodecylamine, or other components in a liquid composition or system, such as an aqueous composition or system. In many cases, the composition of the invention may be solubilized by simple agitation. Dyes or fragrances may also be added for appropriate applications such as toilet waters.

A composition of the present invention may also be prepared in solid form. For example, the ionene polymer and/or salt of dodecylamine may be formulated as a powder or tablet using means known in the art. The tablets may contain a variety of components or excipients known in the tableting art such as dyes or other coloring agents, perfumes or fragrances, as fillers, binders, glidants, lubricants, or antiadherents may. These latter components may be included to improve tablet properties and/or the tableting process.

The following examples are intended to illustrate, not limit, the invention.

EXAMPLE 1

A composition of the invention, was prepared by combining 10.00 percent by weight glacial acetic acid, 23.00 percent by weight dodecylamine acetate, 33.00 percent by weight of propionic acid and 34.00 percent by weight of WSCP® product, an ionene polymer. The acetic acid was charged to a jacketed reaction vessel, stirred and molten dodecylamine added and the mixture stirred for approximately one-half hour. The propionic acid was then added with stirring for an additional one-half hour. The reaction vessel was cooled to absorb any excess heat given off during the neutralization reaction. The WSCP® product was then added and the mixture stirred for another hour.

EXAMPLE 2

Another composition of the invention was prepared according Example 1 by substituting BUSAN® 1055 product, an ionene polymer, for the WSCP® product.

EXAMPLE 3

A composition of the invention, was prepared by combining 19.00 percent by weight glacial acetic acid, 14.00 percent by weight dodecylamine acetate, 33.00 percent by weight of propionic acid and 34.00 percent by weight of WSCP® product, an ionene polymer. The acetic acid was charged to a jacketed reaction vessel, stirred and molten dodecylamine added and the mixture stirred for approximately one-half hour. The propionic acid was then added with stirring for an additional one-half hour. The reaction vessel was cooled to absorb any excess heat given off during the neutralization reaction. The WSCP® product was then added and the mixture stirred for another hour.

Bacteria:

Test Method: The following method effectively defines the ability of a chemical compound to inhibit bacterial adhesion, or attack the formation of existing attached microorganisms, on various types of surfaces. As an overview, bioreactors were constructed in which approximately 1 in.×3 in. slides (glass, stainless steel, or polystyrene) were fixed to the edge of the bioreactor. The lower ends (approx. 2 in.) of the slides dipped into a bacterial growth medium (pH 7) within the bioreactor which contained a known concentration of the test chemical. Following inoculation with known bacterial species, the test solutions were stirred continuously for 3 days. Unless otherwise indicated in the results below, the medium within the bioreactor was turbid by the end of three days. This turbidity indicated that the bacteria proliferated in the medium despite the presence of the chemical tested. This also shows that the chemical, at the concentration tested, showed substantially no biocide (bactericidal) activity. A staining procedure was then used on the slides in order to determine the amount of bacteria attached to the surfaces of the slides.

Construction of Bioreactors: The bioreactors comprised a 400 ml glass beaker over which a lid (cover from a standard 9 cm diameter glass petri dish) was placed. With the lid removed, slides of the material of choice were taped at one end with masking tape and suspended inside the bioreactor from the top edge of the beaker. This allows the slides to be submerged within the test medium. Typically, six slides (replicates) were uniformly spaced around the bioreactor. The score presented below are the average of the six replicates. A magnetic stirring bar was placed in the bottom of the unit, the lid positioned, and the bioreactor autoclaved. Three different types of material were used as slides, stainless steel, glass, and polystyrene.

Bacterial Growth Medium: The liquid medium utilized in the bioreactors was described previously by Delaquis, et al., "Detachment Of *Pseudomonas fluorescens* From Biofilms On Glass Surfaces In Response To Nutrient Stress", Microbial Ecology 18:199–210, 1989. The composition of the medium was:

| Glucose | 1.0 g |
|---|---|
| $K_2HPO_4$ | 5.2 g |
| $KH_2PO_4$ | 2.7 g |
| NaCl | 2.0 g |
| $NH_4Cl$ | 1.0 g |
| $MgSO_4.7H_2O$ | 0.12 g |
| Trace Element | 1.0 mL |
| Deionized $H_2O$ | 1.0 L |
| Trace Element Solution: | |
| $CaCl_2$ | 1.5 g |
| $FeSO_4.7H_2O$ | 1.0 g |
| $MnSO_4.2H_2O$ | 0.35 g |
| $NaMoO_4$ | 0.5 g |
| Deionized $H_2O$ | 1.0 L |

The medium was autoclaved and then allowed to cool. If a sediment formed in the autoclaved medium, the medium was resuspended by shaking before use.

Preparation of Bacterial Inocula: Bacteria of the genera Bacillus, Flavobacterium, and Pseudomonas were isolated from a paper mill slime deposit and maintained in continuous culture. The test organisms were separately streaked onto plate count agar and incubated at 30° C. for 24 hours. With a sterile cotton swab, portions of the colonies were removed and suspended in sterile water. The suspensions were mixed very well and were adjusted to an optical density of 0.858 (Bacillus), 0.625 (Flavobacterium), and 0.775 (Pseudomonas) at 686 nm.

Biofilm Production/Chemical Testing: To four separate bioreactors was added 200 ml of the sterile medium prepared above. Chemicals to be evaluated as biodispersants were first prepared as an aqueous stock solution. A 1.0 ml aliquot of the stock solution was added to the bioreactor using moderate, continuous magnetic stirring. This provided an initial concentration of 100 ppm for the test compound. One bioreactor (Control) contains no test compound. Aliquots (0.5 ml) from each of the three bacterial suspensions were then introduced into each bioreactor. The bioreactors were then provided with continuous stirring for three days to allow for an increase in bacterial population and deposition of cells onto the surfaces of the slides.

Evaluation of Results: The composition described above was evaluated using the procedure described above.

After 48 h or 168 h (1 week) of incubation at 26–28 C., the slides were removed from the bioreactors and were positioned vertically to permit air drying. The degree of adhesion of bacteria to the test surface was then estimated using a staining procedure. The slides were briefly flamed in order to fix the cells to the surface, and then transferred for two minutes to a container of Gram Crystal Violet (DIFCO Laboratories, Detroit, Mich.). The slides were gently rinsed under running tap water, and then carefully blotted. The degree of bacterial adhesion was then determined by a quantitative method of evaluation.

Evaluation of Bacterial Adhesion:

The pair of glass slides, the pair of stainless steel slides, and the pair of polystyrene slides corresponding to each treatment were placed each in Petri plate with 10 mL ethanol (technical) to remove the crystal violet staining the cells attached to the slides. A 1 mL aliquot of the crystal violet ethanol solution obtained in each Petri plate was transferred each to a test tube with 9 mL of deionized sterile water (1/10 dilution). The blank for calibration of the optical instrument used for the evaluation was a solution of 1 mL of ethanol in 9 mL of deionized sterile water. The absorbance (AB) of each solution was determined using a spectrophotometer (Spectronic 21, Bausch and Lomb) at a wavelength of 586 nm. The reduction of bacterial attachment (RBA) was calculated:

RBA (%)=100 [(AB control—(AB treatment–AB blank) \AB control]

90 or >90% RBA=essentially no bacterial adhesion
89–70% RBA=scant
69–50% RBA=moderate
49–30% RBA=moderate
29 or <29% RBA moderate The results are shown in the following Table.

| Compound | RBA glass (%) | RBA stainless steel (%) | RBA polystyrene (%) |
|---|---|---|---|
| Control | 0 | 0 | 0 |
| Example 3 | 98 | 71 | 88 |

Algae:

Test Method: The following method effectively defines the ability of a chemical compound to inhibit algal adhesion, or attack the formation of existing attached microorganisms, on various types of surfaces. As an overview, bioreactors were constructed in which approximately 1 in.×3 in. slides (glass or stainless steel) were fixed to the edge of the bioreactor. The lower ends (approx. 2 in.) of the slides dipped into an algal growth medium within the bioreactor which contained a known concentration of the test chemical. Following inoculation with known algal species, the test solutions were stirred continuously for 3 days. Unless otherwise indicated in the results below, the medium within the bioreactor was turbid by the end of three days. This turbidity indicated that the algae proliferated in the medium despite the presence of the chemical tested. This also shows that the chemical, at the concentration tested, showed substantially no biocide (algal) activity. A staining procedure was then used on the slides in order to determine the amount of algae attached to the surfaces of the slides.

Construction of Bioreactors: The bioreactors comprised a 400 ml glass beaker over which a lid (cover from a standard 9 cm diameter glass petri dish) was placed. With the lid removed, slides of the material of choice were taped at one end with masking tape and suspended inside the bioreactor from the top edge of the beaker. This allows the slides to be submerged within the test medium. Typically, four slides (replicates) were uniformly spaced around the bioreactor. The score presented below are the average of the four replicates. A magnetic stirring bar was placed in the bottom of the unit, the lid positioned, and the bioreactor autoclaved. Three different types of material were used as slides, stainless steel and glass.

Algal Growth Medium: The liquid medium utilized in the bioreactors was Allen Medium as described previously by Richard C. Starr and Jeffrey A. Zeikus in "UTEX—The culture collection of Algae at the University of Texas at Austin," J. of Phycology, Vol. 23, p.36–37 (1978). The composition of the medium was:

|  |  |
| --- | --- |
| Distilled water | 963 mL |
| NaNO$_3$ | 1.5 g | to which was added the following stock solutions:

| mL | stock solution | g/200 mL H$_2$O |
| --- | --- | --- |
| 5 | K$_2$HPO$_4$ | 1.5 |
| 5 | MgSO$_4$7H$_2$O | 1.5 |
| 5 | Na$_2$CO$_3$ | 0.8 |
| 10 | CaCl$_2$2H$_2$O | 0.5 |
| 10 | Na$_2$SiO$_3$9H$_2$O | 1.16 |
| 1 | citric acid | 1.2 |
| 1 | PIV metal solution |  |

The pH of the medium was 7.8.

Algal Inocula: Algal species *Chlorella vulgaris* was used.

Biofilm Production/Chemical Testing: To four separate bioreactors was added 200 ml of the sterile medium prepared above. Chemicals to be evaluated as biodispersants were first prepared as an aqueous stock solution. A 1.0 ml aliquot of the stock solution was added to the bioreactor using moderate, continuous magnetic stirring. This provided an initial concentration of 100 ppm for the test compound. One bioreactor (Control) contains no test compound. Aliquots (0.5 ml) of the algal suspension was then introduced into each bioreactor. The bioreactors were then provided with continuous stirring for three days to allow for an increase in algal population and deposition of cells onto the surfaces of the slides.

Evaluation of Results: The composition described above was evaluated using the procedure described above.

After 48 h or 168 h (1 week) of incubation at 26–28 C., the slides were removed from the bioreactors and were positioned vertically to permit air drying. The degree of adhesion of algae to the test surface was then estimated using a staining procedure. The slides were briefly flamed in order to fix the cells to the surface, and then transferred for two minutes to a container of Gram Crystal Violet (DIFCO Laboratories, Detroit, Mich.). The slides were gently rinsed under running tap water, and then carefully blotted. The degree of algal adhesion was then determined by a quantitative method of evaluation.

Evaluation of Algal Adhesion:

The pair of glass slides and the pair of stainless steel slides were placed in Petri plate with 10 mL ethanol (technical) to remove the crystal violet staining the cells attached to the slides. A 1 mL aliquot of the crystal violet ethanol solution obtained in each Petri plate was transferred each to a test tube with 9 mL of deionized sterile water (1/10 dilution). The blank for calibration of the optical instrument used for the evaluation was a solution of 1 mL of ethanol in 9 mL of deionized sterile water. The absorbance (AB) of each solution was determined using a spectrophotometer (Spectronic 21, Bausch and Lomb) at a wavelength of 586 nm. The reduction of algal attachment (RAA) was calculated:

RAA (%)=100[(AB control−AB treatment)\AB control]

90 or >90% RBA essentially no algal adhesion

89–70% RAA=scant

69–50% RAA=moderate

49–30% RAA=moderate 29 or <29% RAA=moderate

The results are shown in the following Table.

| Compound | RAA glass (%) | RAA stainless steel (%) |
| --- | --- | --- |
| Control | 0 | 0 |
| Example 3 | 92 | 95 |

The invention claimed is:

1. A method to inhibit bacteria from adhering to a submergible surface comprising the step of contacting the submergible surface with an ionene polymer and a salt of dodecylamine in a combined amount effective to inhibit bacteria from adhering to the submergible surface.

2. A method of claim 1, wherein the submergible surface is a ship hull, a boat hull, a marine structure, a tooth surface, a medical implant surface, or a surface of an aqueous system.

3. A method for controlling biofouling of an aqueous system comprising the step of adding to the aqueous system an ionene polymer and a salt of dodecylamine in a combined amount effective to inhibit bacteria from adhering to a submerged surface within the aqueous system.

4. A method of claim 3, wherein the addition step comprises adding a sufficient combined amount of the ionene polymer and the salt of dodecylamine to the aqueous system to reduce any existing biofouling in the aqueous system.

5. A method of claim 4, wherein the aqueous system is an industrial water system.

6. A method of claim 5, wherein the industrial water system is selected from a cooling water system, a metal working fluid system, a papermaking water system, and a textile manufacture water system.

7. A method of claim 4, wherein the aqueous system is a recreational water system.

8. A method of claim 7, wherein the recreational water system is selected from a swimming pool, a spa, a fountain, an ornamental pond, an ornamental pool, and an ornamental stream.

9. A method of claim 4, wherein the aqueous system is a sanitation water system.

10. A method of claim 9, wherein the sanitation water system is selected from a toilet water system, a water treatment system, and a sewage treatment system.

11. A method of claim 4, further comprising the step of adding an effective amount of a biocide to the aqueous system to control the growth of a microorganism in the aqueous system.

12. A method of claim 11, wherein the biocide is added prior to the ionene polymer and the salt of dodecylamine to substantially reduce any existing biofouling in the aqueous system and the combination of the ionene polymer and the salt of dodecylamine is added to prevent the adhesion of surviving microorganisms to a submerged surfaces within the aqueous system.

13. A method of claim 11, wherein a biocide is added concurrently with the ionene polymer and the salt of dodecylamine.

14. A method of claim 11, wherein the microorganism is selected from algae, fungi, and bacteria.

15. A method of claim 11, wherein said aqueous system is selected from an industrial water system, a recreational water system, and a sanitation water system.

16. A composition for controlling biofouling of in an aqueous system, comprising an ionene polymer and a salt of dodecylamine in a combined amount effective to inhibit bacteria from adhering to a submergible surface or a submerged surface within an aqueous system.

17. A composition of claim 16, further comprising a biocide in an amount effective to control the growth of a microorganism in the aqueous system.

18. A composition of claim 16, wherein the composition is in liquid form.

19. A composition of claim 16, wherein the composition is in solid form.

20. A method of claim 1, wherein the method inhibits bacteria from adhering to the submergible surface without substantially killing the bacteria.

21. A method of claim 1, wherein the combined amount is a synergistically effective amount.

22. A method of claim 3, wherein the method inhibits bacteria from adhering to the submergible surface without substantially killing the bacteria.

23. A method of claim 3, wherein the combined amount is a synergistically effective amount.

24. A composition of claim 16, wherein the method inhibits bacteria from adhering to the submergible surface without substantially killing the bacteria.

25. A composition of claim 16, wherein the combined amount is a synergistically effective amount.

* * * * *